(12) United States Patent
Millequant et al.

(10) Patent No.: US 6,312,677 B1
(45) Date of Patent: *Nov. 6, 2001

(54) COSMETIC COMPOSITION BASED ON NONIONIC SURFACTANTS AND CATIONIC OR AMPHOTERIC SUBSTANTIVE POLYMERS AND ITS USE AS A DYEING OR BLEACHING VEHICLE

(75) Inventors: Jean Marie Millequant, Saint Maur; Françoise Boudy, Paris, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/424,600

(22) Filed: Apr. 17, 1995

Related U.S. Application Data

(63) Continuation of application No. 08/020,972, filed on Feb. 22, 1993, now abandoned.

(30) Foreign Application Priority Data

Feb. 21, 1992 (FR) .................................................. 92 02051

(51) Int. Cl.$^7$ ............................... A61K 7/06; A61K 7/13; A61K 7/08; C09B 67/00

(52) U.S. Cl. ...................... 424/70.17; 424/401; 424/70.1; 424/70.11; 424/70.12; 424/70.14; 424/70.19; 424/70.31; 8/405; 8/406; 8/408; 8/431; 8/552

(58) Field of Search .............................. 424/70.19, 70.31, 424/70.1, 70.28, 70.22, 401, 70.11, 70.12, 70.14, 70.17; 8/405, 406, 408, 431, 552

(56) References Cited

U.S. PATENT DOCUMENTS

| | | | |
|---|---|---|---|
| 4,201,766 | * 5/1980 | Grollier | 424/71 |
| 4,371,517 | * 2/1983 | Vanlerberghe et al. | |
| 4,381,919 | * 5/1983 | Jacquet | 424/70 |
| 4,608,250 | * 8/1986 | Jacquet | 424/71 |
| 4,698,065 | 10/1987 | Hoeffkes et al. | 8/406 |
| 4,702,906 | * 10/1987 | Jacquet | 424/70 |
| 4,865,618 | 9/1989 | Junino et al. | 8/411 |
| 4,970,066 | * 11/1990 | Grollier | 424/71 |
| 5,976,195 | * 11/1999 | De La Mettrie et al. | |

FOREIGN PATENT DOCUMENTS

| | | |
|---|---|---|
| 29 36 934 | 3/1980 | (DE) . |
| 221922 | 5/1985 | (DE) . |
| 271219 | 8/1989 | (DE) . |
| 0 428 441 | 5/1981 | (EP) . |
| 0 216 334 | 4/1987 | (EP) . |
| 0 366 542 | 5/1990 | (EP) . |
| 0 376 078 | 7/1990 | (EP) . |
| 0 424 261 | 4/1991 | (EP) . |

OTHER PUBLICATIONS

Griffin, J. Soc. Cosm. Chem., vol. 5, pp 249–56 (1954).*

* cited by examiner

Primary Examiner—Thurman K. Page
Assistant Examiner—Brian K. Seidleck
(74) Attorney, Agent, or Firm—Jacobson Holman, PLLC

(57) ABSTRACT

Cosmetic composition based on nonionic surfactants and cationic or amphoteric substantive polymers and its use as a dyeing or bleaching vehicle. The invention relates to a cosmetic composition containing, in a cosmetically acceptable medium:

a) 14 to 50% of a mixture of nonionic surfactants chosen from oxyethylenated and/or oxypropylenated and/or polyglycerolated fatty alcohols which are linear or branched, the mixture comprising at least one surfactant A whose HLB in the sense used by Griffin is not less than 14, present at a weight concentration [A], and a nonionic surfactant B whose HLB value in the sense used by Griffin is not less than 1 and is less than 10, present in a weight quantity [B], more than one half of the nonionic surfactants present satisfying the inequality:

$$0.5 \leq R \leq 1.6$$

in which R denotes the ratio $$R = \frac{\sum (nC_A \times [A])}{\sum (nC_B \times [B])} = \frac{\text{Sum of the products } nC_A \times [A]}{\text{Sum of the products } nC_B \times [B]}$$

in which:

$nC_A$ is the number of carbon atoms in the fatty chain of the surfactant A and $nC_B$ the number of carbon atoms in the fatty chain of the surfactant B;

b) 0.05 to 10% of a cationic or amphoteric substantive polymer, the composition being stable at room temperature and at a pH above or equal to 5.5.

19 Claims, No Drawings

COSMETIC COMPOSITION BASED ON NONIONIC SURFACTANTS AND CATIONIC OR AMPHOTERIC SUBSTANTIVE POLYMERS AND ITS USE AS A DYEING OR BLEACHING VEHICLE

This application is a continuation of application Ser. No. 08/020,972, filed Feb. 22, 1993, now abandoned.

The present invention relates to a new cosmetic composition based on nonionic surfactants and cationic or amphoteric substantive polymers, to the use of this composition for the preparation of compositions for dyeing or bleaching keratinous fibers and to the dyeing or bleaching processes employing such compositions.

Compositions containing one or more nonionic surfactants, including especially polyoxyethylenated or polyglycerolated nonionic compounds, are known.

It is also known that cationic polymers enable the cosmetic condition of the hair, especially disentangling, to be improved. As a result, in cosmetic compositions containing nonionic surfactants used as a dyeing and bleaching vehicle, an effort is made to use cationic polymers for the purpose of imparting good cosmetic properties, in particular those of disentangling, to the dyed and bleached keratinous fibers.

It has, however, been found that some cationic polymers created problems of compatibility with nonionic vehicles, manifesting themselves in a phase separation during storage, a modification of the consistency and foaming properties.

This problem had been resolved, in particular, in FR-A-2,502,949 in the case of oxidation dyeing compositions employing an oxidizing solution, by the use of a process consisting in storing separately, on the one hand the cationic polymer in the oxidizing solution containing, in particular, hydrogen peroxide, and on the other hand the dyeing composition containing the dyes and the nonionic surfactants. Mixing of the two compositions was performed at the time of use.

The Applicant has discovered, and this forms the subject of the invention, that it was possible to avoid the separation of the composition used as a vehicle, especially for dyeing or bleaching, into several phases, or the precipitation of the ingredients of the vehicle, by introducing, into a composition containing particular nonionic surfactants, cationic or amphoteric substantive polymers which are supposedly incompatible with the nonionic medium of said composition so as to obtain a composition which is stable to temperature and over time.

The subject of the invention is hence a cosmetic composition containing, in a cosmetically acceptable medium, a mixture of particular nonionic surfactants and cationic or amphoteric type substantive polymers.

Another subject of the invention consists of the use of this composition as a vehicle in dyeing or bleaching compositions.

The subject of the invention is also the dyeing or bleaching compositions thereby obtained, as well as their use for dyeing and bleaching hair.

Other subjects of the invention will become apparent on reading the description and the examples which follow.

The composition according to the invention is essentially distinguished by the fact that it contains, in a cosmetically acceptable medium:
a) 14 to 50% and preferably 20 to 50% by weight of a mixture of nonionic surfactants chosen from fatty alcohols and oxyethylenated and/or oxypropylenated and/or polyglycerolated fatty alcohols which are linear or branched and which can contain aromatic units, the mixture comprising at least one surfactant A having an HLB in the sense used by Griffin of not less than 14, this surfactant being present in a weight quantity equal to [A], and at least one nonionic surfactant B whose HLB in the sense used by Griffin is not less than 1 and is less than 10, present in a weight quantity [B], the ratio $$R = \frac{\sum (nC_A \times [A])}{\sum (nC_B \times [B])} = \frac{\text{Sum of the products } nC_A \times [A]}{\text{Sum of the products } nC_B \times [B]}$$

in which:
$nC_A$ and $nC_B$ denote, respectively, the number of carbon atoms in the fatty chain of the surfactants A and B, being such that:
$0.5 \leq R \leq 1.6$, more than 50% and preferably at least 52% of the nonionic surfactants present satisfying the inequality for R;
b) 0.05 to 10% by weight of a cationic or amphoteric substantive polymer, said composition being stable at room temperature
and at a pH equal to or above 5.5.

The nonionic surfactants which are useable according to the invention of type A and which possess an HLB in the sense used by Griffin of not less than 14 are preferably chosen from fatty alcohols whose fatty chain contains a number of carbon atoms from 12 to 30 ($12 \leq nC_A \leq 30$), and the type B surfactants having an HLB in the sense used by Griffin of between 1 and 10 are preferably chosen from fatty alcohols whose fatty chain contains a number of carbon atoms from 10 to 50 ($10 \leq nC_B \leq 50$).

Among type A surfactants, there may be mentioned, more especially:
oxyethylenated oleocetyl alcohol containing 30 mol of ethylene oxide
$nC_A=17$ (average value)
HLB=16.5
oxyethylenated lauryl alcohol ($C_{12}$–$C_{14}$/55–45%) containing 12 mol of ethylene oxide
$nC_A=12.5$
HLB=14
oxyethylenated lauryl alcohol containing 23 mol of ethylene oxide
$nC_A=12$
HLB=16.6
oxyethylenated cetyl/stearyl alcohol containing 15 mol of ethylene oxide
$nC_A=17$
HLB=14.5
oxyethylenated stearyl alcohol containing 100 mol of ethylene oxide
$nC_A=18$
HLB=18.8
oxyethylenated isostearyl alcohol containing 20 mol of ethylene oxide
$nC_A=18$
HLB=14.9
oxyethylenated behenyl alcohol containing 20 mol of ethylene oxide
$nC_A=22$
HLB=16.5
oxyethylenated $C_{30}$ primary alcohol containing 40 mol of ethylene oxide
$nC_A=30$ HLB=16.1
oxyethylenated octylphenols containing 11 to 50 mol of ethylene oxide, oxyethylenated nonylphenols containing 12 to 50 mol of ethylene oxide.

Among type B fatty alcohols, there may be mentioned, more especially:
oxyethylenated decyl alcohol containing 3.5 mol of ethylene oxide
$nC_B=10.4$
HLB=8.5
oleyl alcohol containing 70% of $C_{18}$
$nC_B=17.5$
HLB=1
lauryl alcohol
$nC_B=12$
HLB=1
cetyl/stearyl (50:50) alcohol
$nC_B=17$
HLB=1
oxyethylenated isostearyl alcohol containing 2 mol of ethylene oxide
$nC_B=18$
HLB=6.5
oxyethylenated oleyl alcohol containing 3 mol of ethylene oxide
$nC_B=18$
HLB=6.5
oxyethylenated lauryl alcohol containing 4 mol of ethylene oxide
$nC_B=12$
HLB=9.7
oxypropylenated lauryl alcohol containing 3 mol of propylene oxide
$nC_B=12$
HLB close to 1
oxyethylenated $C_{50}$ primary alcohol containing 4 mol of ethylene oxide
$nC_B=50$
HLB=4
polyglycerolated oleyl alcohol containing 2 mol of glycerol
$nC_B=18$
HLB=7.1
oxyethylenated octylphenols containing less than 4.5 mol of ethylene oxide
oxyethylenated nonylphenols containing less than 5 mol of ethylene oxide.

The HLB value according to Griffin is defined in J.Soc.Cosm.Chem. 1954 (volume 5), pages 249–256.

The composition according to the invention can contain, in a proportion of less than 50% and, in particular, not exceeding 48% of the total of surfactants present, nonionic surfactants possessing an intermediate HLB according to Griffin of between 10 and 14.

Among these surfactants, there may be mentioned oxyethylenated decyl alcohol containing 5.5 mol of ethylene oxide (HLB=11.5), oxyethylenated nonylphenol containing 6 mol of ethylene oxide (HLB=11) and oxyethylenated $C_{30}$ primary alcohol containing 10 mol of ethylene oxide (HLB=10).

The substantive character of the cationic or amphoteric polymers used according to the invention is determined by the test using the dye Acid Red 80, according to RICHARD J. CRAWFORD, Journal of the Society of Cosmetic Chemists, 1980-31-(5)-pages 273 to 278.

These polymers are, inter alia, polymers which are incompatible with a nonionic vehicle not corresponding to the definition according to the invention.

The incompatible character may be determined, in particular, by introducing 1% of active substances of this substantive polymer into a nonionic medium such as that described in FR 2,502,949. The production of a more or less marked cloudy appearance and possibly even of a precipitate and/or the separation of the composition into two phases is considered to the be criterion of incompatibility.

The substantive polymers are chosen especially from polymers containing primary, secondary, tertiary and/or quaternary amine groups, forming part of the polymer chain or linked directly to the latter, and having a molecular weight of between 500 and approximately 5,000,000, and preferably between 1000 and 3,000,000.

Among these polymers, there may be mentioned, more especially, quaternized proteins, polymers of the polyamine, polyaminoamide or poly(quaternary ammonium) family and cationic polysiloxanes.

A. The quaternized proteins are, in particular, chemically modified polypeptides bearing quaternary ammonium groups at the end of the chain or grafted onto the latter. Among these proteins, there may be mentioned, in particular:
collagen hydrolysates bearing triethylammonium groups, such as the products sold by the company MAYBROOK under the name "QUAT-PRO E" and designated in the CTFA Dictionary "Triethonium Hydrolyzed Collagen Ethosulfate";
collagen hydrolysates bearing trimethylammonium and dimethylstearylammonium chloride groups, sold by the company MAYBROOK under the name "QUAT-PRO S" and designated in the CTFA Dictionary "Steartrimonium Hydrolyzed Collagen";
animal protein hydrolysates bearing dimethylbenzylammonium groups, such as the products sold by the company CRODA under the name "CROTEIN BTA" and designated in the CTFA Dictionary "Benzyltrimonium Hydrolyzed Animal Protein";
protein hydrolysates bearing on the polypeptide chain quaternary ammonium groups containing at least one alkyl radical having from 1 to 18 carbon atoms.

Among these protein hydrolysates, there may be mentioned, inter alia:
CROQUAT L, in which the polypeptide chain has an average molecular weight of approximately 2500 and in which the quaternary ammonium group contains a $C_{12}$ alkyl group;
CROQUAT M, in which the polypeptide chain has an average molecular weight of approximately 2500 and in which the quaternary ammonium group contains a $C_{10}$–$C_{18}$ alkyl group;
CROQUAT S, in which the polypeptide chain has an average molecular weight of approximately 2700 and in which the quaternary ammonium group contains a $C_{18}$ alkyl group;
CROQUAT Q, in which the polypeptide chain has an average molecular weight of the order of 12,000 and in which the quaternary ammonium group contains at least one alkyl group having from 1 to 18 carbon atoms;
a soybean quaternized vegetable protein sold under the name CROQUAT SOYA.

These various products are sold by the company CRODA.
a quaternized protein resulting from the condensation of cocamidopropyldimethylamine with a hydrolyzed animal protein, designated in the CTFA Dictionary, 1991 edition, Quaternium 76 Hydrolysed Collagen, sold by the company INOLEX under the name LEXEIN QX 3000.

B. The polymers of the polyamine, polyaminoamide or poly(quaternary ammonium) family which are useable according to the present invention are described, in particular, in the Applicant's French Patents nos. 2,505,348, 2,542,997 and 2,598,613.

Among these polymers, there may be mentioned:

(1) Vinylpyrrolidone/dialkylaminoalkyl acrylate or methacrylate copolymers, quaternized or otherwise, such as the products sold by the company GAF CORPORATION under the name "GAFQUAT", for example "GAFQUAT 734 or 755", or alternatively the products designated "COPOLYMER 845, 958 and 937". These polymers are described in detail in French Patents 2,077,143 and 2,393,573; and the quaternized vinylpyrrolidone/dimethylaminopropylmethacrylamide copolymer such as the product sold by the company GAF under the name "GAFQUAT HS100".

(2) The cellulose ether derivatives containing quaternary ammonium groups described in French Patent 1,492,597, and especially the polymers marketed by the company UNION CARBIDE CORPORATION under the names "JR" (JR 400, JR 125, JR 30M) or "LR" (LR 400, LR 30M). The polymers are also defined in the CTFA Dictionary as quaternary ammonium derivatives of hydroxyethylcellulose subjected to reaction with an epoxide substituted with a trimethylammonium group.

(3) Cationic cellulose derivatives such as cellulose copolymers or cellulose derivatives grafted with a water-soluble quaternary ammonium monomer, and described in greater detail in U.S. Pat. No. 4,131,576, for example hydroxyalkylcelluloses such as hydroxymethyl-, hydroxyethyl- or hydroxypropylcellulose grafted with a methacryloylethyltrimethylammonium, methacrylamidopropyltrimethylammonium or dimethyldiallylammonium salt.

Marketed products corresponding to this definition are, more especially, the products sold by the company NATIONAL STARCH under the names "CELQUAT L 200" and "CELQUAT H 100".

(4) The quaternized polysaccharides described, more especially, in U.S. Pat. Nos. 3,589,578 and 4,031,307, such as the product marketed under the name "JAGUAR C 13 S", sold by the company MEYHALL.

(5) Polymers consisting of piperazinyl units and divalent alkylene or hydroxyalkylene radicals having unbranched or branched chains optionally interrupted by oxygen, sulfur or nitrogen atoms or by aromatic or heterocyclic ring-systems, as well as the oxidation and/or quaternization products of these polymers. Such polymers are described in U.S. Pat. Nos. 3,917,817 and 4,013,787.

(6) Water-soluble polyaminoamides prepared, in particular, by polycondensation of an acid compound with a polyamine. These polyaminoamides may be crosslinked with an epihalohydrin, a diepoxide, a dianhydride, an unsaturated anhydride, a bis-unsaturated derivative, a bis-halohydrin, a bis-azetidinium compound, a bis-haloacyldiamine or a bis(alkyl halide), or alternatively with an oligomer resulting from the reaction of a bi-functional compound which is reactive towards a bis-halohydrin, a bis-azetidinium compound, a bis-haloacyldiamine, a bis (alkyl halide), an epihalohydrin, a diepoxide or a bis-unsaturated derivative; the crosslinking agent being used in proportions ranging from 0.025 to 0.35 mol per amide group of the polyaminoamide.

These polyaminopolyamides may be alkylated or, if they contain one or more tertiary amine functions, quaternized. Such polymers are described especially in U.S. Pat. Nos. 4,172,887 and 4,189,468.

(7) Polyaminoamide derivatives resulting from the condensation of polyalkylenepolyamines with polycarboxylic acids followed by an alkylation with bi-functional agents. There may be mentioned, for example, adipic acid/dialkylaminohydroxyalkyl/dialkylenetriamine polymers in which the alkyl radical contains from 1 to 4 carbon atoms and preferably denotes methyl, ethyl or propyl. Such polymers are described in French Patent 1,583,363.

Among these derivatives, there may be mentioned, more especially, the adipic acid/dimethylaminohydroxypropyl/diethylenetriamine polymers sold by the company SANDOZ under the name "CARTARETINE F, $F_4$ or $F_8$".

(8) Polymers obtained by reaction of a polyalkylenepolyamine containing two primary amine groups and at least one secondary amine group with a dicarboxylic acid chosen from diglycolic acid and saturated aliphatic dicarboxylic acids having from 3 to 8 carbon atoms. The mole ratio of the polyalkylenepolyamine to the dicarboxylic acid is between 0.8:1 and 1.4:1; the polyaminoamide resulting therefrom being reacted with epichlorohydrin in a mole ratio of epichlorohydrin relative to the secondary amine group of the polyaminoamide of between 0.5:1 and 1.8:1. Such polymers are described especially in U.S. Pat. Nos. 3,227,615 and 2,961,347.

Polymers of this type are, in particular, marketed by the company HERCULES INCORPORATED under the name "HERCOSETT 57", or alternatively by the company HERCULES under the name "PD 170" or "DELSETTE 101" in the case of the adipic acid/epoxypropyl/diethylenetriamine copolymer.

(9) Cyclopolymers having a molecular weight of 20,000 to 3,000,000, such as the homopolymers containing as main constituent of the chain units corresponding to the formulae (II) or (II'):

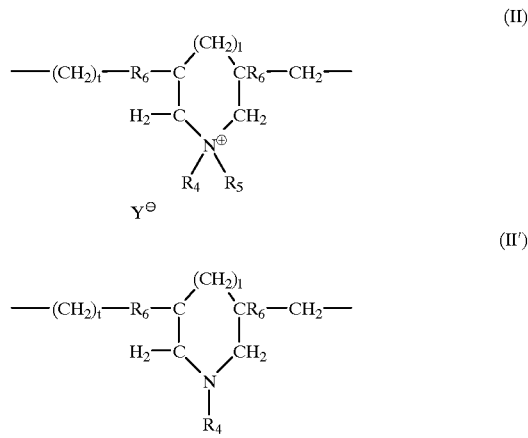

l and t are equal to 0 or 1, and the sum l+t=1;

$R_6$ denotes hydrogen or methyl;

$R_4$ and $R_5$ denote, independently of one another, an alkyl group having from 1 to 22 carbon atoms, a hydroxyalkyl group in which the alkyl group preferably has 1 to 5 carbon atoms or a lower amidoalkyl group, and where $R_4$ and $R_5$, jointly with the nitrogen atom to which they are attached, can denote heterocyclic groups such as piperidyl or morpholinyl, as well as copolymers containing units of formulae (II) or (II') and units derived from acrylamide or from diacetoneacrylamide;

$Y^{\ominus}$ is an anion such as bromide, chloride, acetate, borate, citrate, tartrate, bisulfate, bisulfite, sulfate, phosphate.

Among the polymers defined above, there may be mentioned, more especially, the homopolymer of dimethyl-diallylammonium chloride sold by the company MERCK under the name "MERQUAT 100", having a molecular weight of less than 100,000, and the copolymer of dimethyldiallylammonium chloride and acrylamide having a molecular weight above 500,000 and sold under the name "MERQUAT 550".

These polymers are described, more especially, in French Patent 2,080,759 and its Certificate of Addition no. 2,190,406.

(10) The poly(quaternary ammonium) polymer containing recurring units corresponding to the formula:

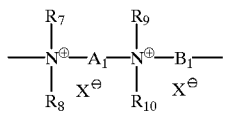
(III)

in which $R_7$ and $R_8$, $R_9$ and $R_{10}$, being identical or different, represent aliphatic, alicyclic or acrylaliphatic radicals containing from 1 to 20 carbon atoms or lower hydroxyalkylaliphatic radicals, or alternatively $R_7$ and $R_8$ and $R_9$ and $R_{10}$, together or separately and with the nitrogen atoms to which they are attached, constitute heterocycles optionally containing a second hetero atom other than nitrogen, or alternatively $R_7$, $R_8$, $R_9$ and $R_{10}$ represent a linear or branched $C_1$–$C_6$ alkyl radical substituted with a nitrile, ester, acyl or amide group or a group

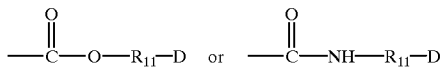

where $R_{11}$ is an alkylene and D a quaternary ammonium group.

$A_1$ and $B_1$ represent polymethylene groups containing from 2 to 20 carbon atoms, which can be linear or branched and saturated or unsaturated, and which can contain, linked to or intercalated in the main chain, one or more aromatic ring-systems or one or more oxygen or sulfur atoms or sulfoxide, sulfone, disulfide, amino, alkylamino, hydroxyl, quaternary amino, ureido, amide or ester groups, and $X^{\ominus}$ denotes an anion derived from an inorganic or organic acid.

$A_1$ and $R_7$ and $R_9$, with the two nitrogen atoms to which they are attached, can form a piperazine ring; in addition, if $A_1$ denotes a saturated or unsaturated, linear or branched alkylene or hydroxyalkylene radical, $B_1$ can also denote a group

in which D denotes:
a) a glycol residue of formula: —O—Z—O— where Z denotes a linear or branched hydrocarbon radical or a group corresponding to the formulae:

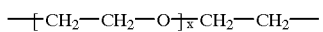

-continued

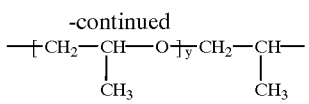

where x and y denote an integer from 1 to 4, representing a defined and unique degree of polymerization, or any number from 1 to 4 representing an average degree of polymerization;

b) a bis-secondary diamine residue such as a piperazine derivative;

c) a bis-primary diamine of formula:

—NH—Y—NH— where Y denotes a linear or branched hydrocarbon radical or alternatively the divalent radical

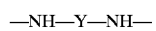

d) a ureylene group of formula:

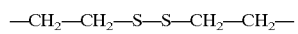

$X^{\ominus}$ is an anion such as chloride or bromide.

These polymers have a molecular mass generally of between 1000 and 100,000.

Polymers of this type are described especially in French Patents 2,320,330, 2,270,846, 2,316,271, 2,336,434 and 2,413,907, and Patents U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) The poly(quaternary ammonium) polymers consisting of units of formula:

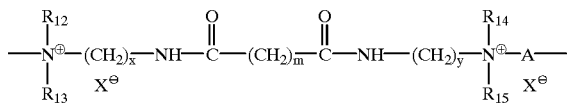

in which
$R_{12}$, $R_{13}$, $R_{14}$ and $R_{15}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH radical,
where p is equal to 0 or an integer between 1 and 6, with the proviso that $R_{12}$, $R_{13}$, $R_{14}$ and $R_{15}$ do not simultaneously represent a hydrogen atom;
x and y, which may be identical or different, are integers between 1 and 6; m is equal to 0 or to an integer between 1 and 34;
x denotes a halogen atom;
A denotes a radical of a dihalide and preferably represents

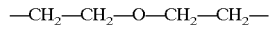

Such compounds are described in greater detail in Application EP-A-122,32 4.

There may, for example, be mentioned, among these compounds, the products "MIRAPOL A 15", "MIRAPOL AD1", "MIRAPOL AZ1" and "MIRAPOL 175" sold by the company MIRANOL.

(12) Homopolymers or copolymers derived from acrylic or methacrylic esters or amides and containing the units:

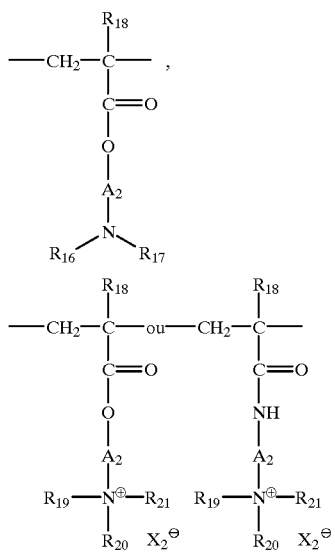

(V)

in which
$R_{18}$ denotes H or $CH_3$;
$A_2$ is a linear or branched alkyl group containing 1 to 6 carbon atoms or a hydroxyalkyl group containing 1 to 4 carbon atoms;
$R_{19}$, $R_{20}$ and $R_{21}$, which may be identical or different, represent an alkyl group having from 1 to 18 carbon atoms or a benzyl radical;
$R_{16}$ and $R_{17}$ represent hydrogen or an alkyl group having from 1 to 6 carbon atoms;
$X^{\ominus}_2$ denotes a methosulfate anion or a halide such as chloride or bromide.

Useable comonomer(s) belong to the family comprising acrylamide, methacrylamide, diacetoneacrylamide, acrylamide and methacrylamide substituted on the nitrogen with lower alkyl groups, acrylic or methacrylic acids or their esters, vinylpyrrolidone, vinyl esters.

Among these compounds, there may be mentioned the copolymer of acrylamide and dimethylaminoethyl methacrylate quaternized with dimethyl sulfate and sold by the company HERCULES under the name "HERCOFLOC", the copolymer of acrylamide and methacryloyloxyethyltrimethylammonium chloride—described in Patent Application EP-A-80,976—and sold by the company CIBA GEIGYC under the name "BINA QAT P100", or alternatively the poly-(methacrylamidopropyltrimethylammonium chloride) sold by the company TEXACO CHEMICALS under the name "POLYMAPTAC", and the methacryloyloxyethyltrimethylammonium methosulfate and its copolymer with acrylamide which are sold by the company HERCULES under the name "RETEN".

(13) Quaternary polymers of vinylpyrrolidone and of vinylimidazole, such as, for example, the products marketed by the company BASF under the names "LUVIQUAT FC 905, FC 550 and FC 370".

(14) Polyamines such as Polyquart H sold by HENKEL, listed under the reference name "POLYETHYLENE GLYCOL (15) TALLOW POLYAMINE" in the CTFA Dictionary.

Other substantive polymers which are useable according to the invention are polyalkylenimines, especially polyethylenimines, polymers containing vinylpyridine or vinylpyridinium units, condensates of polyamines and epichlorohydrin, quaternary polyureylenes and chitin derivatives.

The cationic polysiloxanes are chosen, more especially, from:

(1) the polymers of formula:

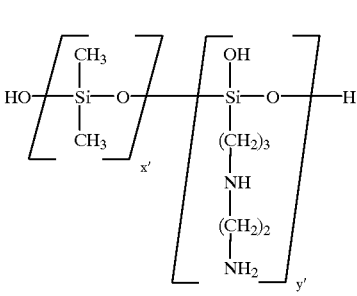

(VI)

in which x' and y' are integers dependent on the molecular weight, which is generally between 5000 and 10,000. These products are designated "Amodimethicone" in the CTFA Dictionary.

(2) the cationic silicon polymers corresponding to the formula:

in which:

G is a hydrogen atom or a phenyl group, OH or a $C_{1-C8}$ alkyl, and preferably methyl, group;

a denotes 0 or an integer from 1 to 3, and preferably 0;

b denotes 0 or 1, and preferably 1;

the sum (n+m) is an integer from 1 to 2000, and preferably from 50 to 150, it being possible for n to denote a number from 0 to 1999, and preferably from 49 to 149, and for m to denote an integer from 1 to 2000, and preferably from 1 to 10;

R' is a monovalent radical of formula $C_qH_{2q}L$, in which q is a number from 2 to 8 and L is chosen from the groups:

—N(R")—CH$_2$—CH$_2$—N(R")$_2$

—N(R")$_2$

—N$^{\oplus}$(R")$_3$A$^-$

—N$^{\oplus}$(R")H$_2$A$^-$

—N(R")CH$_2$—CH$_2$—N$^{\oplus}$(R")H$_2$ A$^-$, in which formulae R" can denote hydrogen, phenyl, benzyl, a saturated monovalent hydrocarbon radical and preferably an alkyl radical having from 1 to 20 carbon atoms, and A$^-$ represents a halide ion such as chloride, bromide, iodide or fluoride.

An especially advantageous product conforming to this definition is the polymer designated "trimethylsilylamodimethicone" corresponding to the formula:

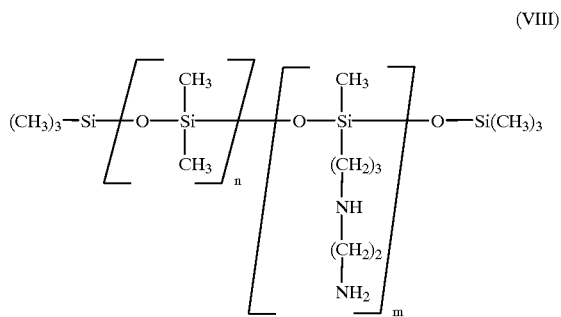
(VIII)

in which n and m have the meanings given above for x' and y' (formula VI). Such polymers are described in Patent Application EP-A-95,238;

(3) the cationic silicone polymers corresponding to the formula:

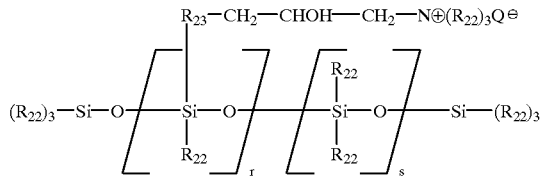
(IX)

in which:

$R_{22}$ denotes a monovalent hydrocarbon radical having from 1 to 18 carbon atoms, and especially an alkyl or alkenyl, and preferably methyl, radical;

$R_{23}$ denotes a divalent hydrocarbon radical, preferably a $C_1$–$C_{18}$ alkylene radical or a divalent $C_1$–$C_{18}$, and preferably $C_1$–$C_8$, alkyleneoxy radical;

$Q^\ominus$ is a halide, and preferably chloride, ion;

r represents an average statistical value from 2 to 20, and preferably from 2 to 8;

a represents an average statistical value from 20 to 200, and preferably from 20 to 50.

Such polymers are described, more especially, in U.S. Pat. No. 4,185,087.

An especially preferred polymer conforming to this class is the polymer sold by the company UNION CARBIDE under the name "UCAR SILICONE ALE 56", the features of which are a flashpoint according to Standard ASTDM-93 of 60° C., a viscosity at a concentration of 35% of active substance and at 25° C. of 0.011 Pa.s and by a total basic number of 0.24 meq/g.

When these silicone polymers are employed, an especially advantageous embodiment is their joint use with nonionic surfactants, and optionally cationic surfactants. It is possible to use, for example, in the compositions according to the invention, the commercial product sold by the company DOW CORNING under the name "CATIONIC EMULSION DC 929", which comprises the amodimethicone of formula (VI), a cationic surfactant corresponding to the formula:

(X)

in which $R_{24}$ denotes a mixture of alkenyl and/or alkyl radicals having from 14 to 22 carbon atoms derived from tallow fatty acids, and a nonionic surfactant of formula:

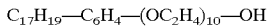
$C_{17}H_{19}$—$C_6H_4$—$(OC_2H_4)_{10}$—OH known by the name "NONOXYNOL 10".

Another composition which is useable in this embodiment of the invention is the composition containing the product sold by the company DOW CORNING under the name "DOW CORNING Q2 7224" containing, in combination, the trimethylsilylamodimethicone of formula (VIII), a nonionic surfactant of formula:

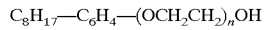
$C_8H_{17}$—$C_6H_4$—$(OCH_2CH_2)_n$OH where n=40 also designated octoxynol-40, another nonionic surfactant of formula;

$C_{12}H_{25}$—$(OCH_2$—$CH_2)_n$OH where n=6 also designated isolaureth-6, and glycol.

The substantive polymers may be chosen from amphoteric polymers, such as amphoteric polymers derived from chitosan or copolymers of diallyldialkylammonium and an anionic monomer.

(1) the amphoteric polymers derived from chitosan are chosen especially from polymers containing units corresponding to the formulae:

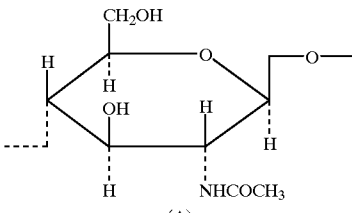
(XI)

(A)

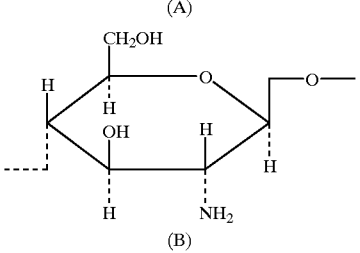

(B)

-continued

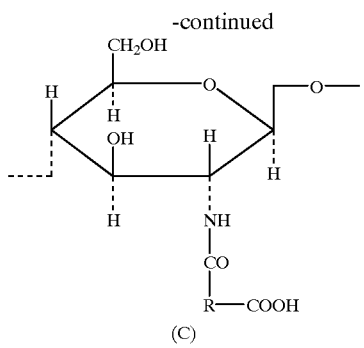

(C)

The unit (A) is present in proportions from 0 to 30%, the unit (B) from 5 to 50% and the unit (C) from 30 to 90% by weight. R represents a linear or branched alkylene group containing from 2 to 5 carbon atoms.

The preferred polymer preferably contains 0 to 20% of unit (A), 40 to 50% of unit (B) and 40 to 50% of unit (C) in which R denotes an alkylene radical, and preferably —CH$_2$—CH$_2$—.

Such polymers are described, more especially, in Patent FR-A-2,137,684.

(2) the amphoteric polymers of diallyldialkylammonium and an anionic monomer are chosen, more especially, from polymers containing approximately 60 to approximately 99% by weight of units derived from a quaternary diallyl-dialkylammonium monomer in which the alkyl groups are chosen independently from alkyl groups having 1 to 18 carbon atoms and in which the anion is derived from an acid having an ionization constant of greater than $10^{-13}$, and 1 to 40% by weight of this polymer of an anionic monomer chosen from acrylic or methacrylic acids, the molecular weight of this polymer being between approximately 50,000 and 10,000,000, determined by gel permeation chromatography. Such polymers are described in Application EP-A-269,243.

Preferred polymers are, inter alia, polymers containing alkyl groups chosen from groups having 1 to 4 carbon atoms, and more especially methyl and ethyl groups.

Among these polymers, copolymers of dimethyldiallylammonium or diethyldiallylammonium chloride and acrylic acid are especially preferred.

As especially preferred products, there may be mentioned the polymer sold by the company CALGON under the name "MERQUAT 280" in the form of an aqueous solution containing 35% of active substance, this polymer being a copolymer of diallyldimethylammonium chloride and acrylic acid in the proportions 80:20, the viscosity in a module 4 Brookfield LVF viscometer being between 4000 and 10,000 cps, the molecular weight being approximately equal to 1,300,000.

More especially preferred substantive polymers according to the invention are chosen from:

a) the poly(quaternary ammonium) polymers prepared and described in French Patent 2,270,846, consisting of recurring units corresponding to the formula:

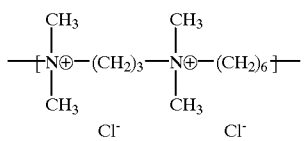

b) the copolymer of the diallyldimethylammonium chloride and acrylic acid (80/20) sold by the company CALGON under the name MERQUAT 280;

c) the homopolymer of dimethyldiallylammonium chloride sold by the company MERCK under the name MERQUAT 100;

d) the quaternized cellulose ether derivatives sold by the company UNION CARBIDE under the name JR;

e) the copolymer of vinylpyrrolidone and methacrylamidopropyltrimethylammonium chloride (85:15) sold by the company GAF under the name GAFQUAT HS 100.

The cosmetic compositions defined above possess a viscosity which enables them to be applied, in particular, to the scalp; this viscosity does not increase substantially on storage. It possesses a consistency of gelled cream or gel into which a larger quantity of starting materials or adjuvants, and in particular of active substances, especially dyes, may be introduced.

The composition according to the invention is especially advantageous in its use as a vehicle for a composition for dyeing or bleaching keratinous fibers, especially hair.

It was possible to observe that these new vehicles according to the invention possess greater ease of mixing with the oxidizing solution, permitting higher dilutions without significant loss of consistency and foaming properties.

The composition contains, in this embodiment, oxidation dye precursors which are known per se, forming dyes following a process of oxidative condensation of these dye precursors, where appropriate in the presence of couplers or modifiers, or indole precursors generating melanin type pigments under the action of an oxidizing agent, and/or direct dyes.

The oxidation dye precursors which are useable are known per se. Reference may be made, more especially, to ZVIAK, Science des Traitements capillaires [Hair Treatment Science] 1988, pages 235 to 287. The compounds in question are, more especially, diamines or amino-phenols containing functional amino and OH groups at the para or ortho position; the couplers or modifiers are, more especially, meta-diamines, meta-aminophenols or meta-diphenols.

These compositions can also contain, in addition to oxidation dye precursors, direct dyes which enable the hues to be enriched, such as azo dyes, anthraqiinone dyes, nitro derivatives of the benzene series, indamines, indoaniline and indophenols.

The indole dyes generating melanin type pigments are, more especially, described in French Patents and Patent Applications FR-A-2,593,061, 2,593,062, 2,595,245, 2,606, 636 and 2,636,237, and European Patent Applications EP-A-425,345 and EP-A-424,261. More especially preferred indole compounds are chosen from 5,6-dihydroxyindole and its derivatives and 6- and 7-monohydroxyindoles.

The dyeing compositions containing the vehicle according to the invention do not contain an oxidizing agent, but are generally used jointly with an oxidizing solution for the purpose of developing the coloration.

The Applicant found that, by means of the new vehicle according to the invention, mixing with the oxidizing solution was much easier and permitted higher dilutions without significant loss of the consistency and foaming properties of the composition.

The cosmetically acceptable medium of the compositions according to the invention is generally an aqueous medium or a mixture of water with a water-miscible organic solvent. Among these solvents, there may be mentioned lower aliphatic alcohols such as ethyl alcohol, propyl or isopropyl alcohol, glycols and glycol ethers such as propylene glycol, hexylene glycol, diethylene glycol, dipropylene glycol, ethylene glycol monomethyl, -ethyl and -butyl ethers, diethylene glycol monoethyl ether as well as mixtures thereof.

Especially preferred solvents are ethyl alcohol, propylene glycol and ethylene glycol monobutyl ether. These solvents may be used in weight proportions which can reach 20% by weight relative to the total weight of the composition.

The compositions according to the invention can also contain adjuvants such as alkalinizing agents, preservatives, sequestering agents, perfumes, sunscreen agents, fatty amides, natural or synthetic sterols, $C_{10}$–$C_{18}$ fatty acids, polymers other than the substantive polymers according to the invention or thickeners, with the proviso that they do not destabilize the vehicle.

The composition does not contain alkyl sulfates or alkyl ether sulfates liable to destabilize the composition.

Alkalinizing agents are generally used in quantities sufficient to adjust the pH to a value above or equal to 5.5. These alkalinizing agents are chosen, more especially, from sodium hydroxide, potassium hydroxide, ammonia solution, monoethanolamine, diethanolamine, triethanolamine, mono- or diisopropanolamine, 2-amino-2-methyl-1,3-propanediol, 2-amino-2-methyl-1-propanol and mixtures thereof.

The fatty amides are, more especially, chosen from oleic or lauric diethanolamide, coconut mono- or diethanolamide, and oxyethylenated ($C_{13}$–$C_{15}$) alkyl ether carboxylic acid monoethanolamide containing 2 mol of ethylene oxide, sold by the company CHEM Y under the name AMINOL A15.

It is also possible to use polymers and thickeners such as, more especially:

the monobutyl ester of methyl vinyl ether/maleic anhydride copolymer, sold by the company GAF under the name GANTREZ ES425;

polyacrylamidomethylpropanesulfonic acid sold by the company HENKEL under the name COSMEDIA POLYMER HSP 1180;

vinyl acetate/vinyl tert-butylbenzoate/crotonic acid (65:25:10) terpolymer as described in French Patent 2,439,798, 100% neutralized with 2-amino-2-methyl-1-propanol;

silicas such as the hydrophobic silica sold by the company DEGUSSA under the name AEROSIL R 972, or the hydrophilic silica sold by the company WACKER CHEMIE under the name SILICE HDK-N 20E;

crosslinked polyacrylic acids such as the CARBOPOLS sold by the company GOODRICH.

For bleaching hair, bleaching agents known per se, such as hydrogen peroxide, persulfates, perborates and alkali metal percarbonates, are used.

Such agents are, more especially, described in ZVIAK, Science des Traitements capillaires [Hair Treatment Science], 1988.

Employing hydrogen peroxide, compositions which can contain up to 60 volumes of hydrogen peroxide, and preferably 10 to 40 volumes, are generally used.

The subject of the invention is also a hair dyeing or bleaching process, wherein a composition as defined above, containing the vehicle according to the invention, is applied to the hair in a sufficient quantity to produce either dyeing or bleaching.

When used for dyeing, this composition is generally diluted at the time of use with the oxidizing solution in a ratio ranging from 0.5 to 5, and preferably from 1 to 3, by volume. The composition is allowed to act for a time of between 5 and 45 minutes approximately, and preferably between 15 and 30 minutes, and the hair is then rinsed.

When used for bleaching, it does not contain dyes or precursors, and is applied directly to the hair in a quantity and for a sufficient period to bleach the hair.

The examples which follow are intended as illustrations of the invention, no limitation being implied.

EXAMPLE 1

| | |
|---|---|
| Oxyethylenated oleocetyl alcohol containing 30 mol of ethylene oxide ($nC_A$ = 17 – HLB = 16.5) | 7 g |
| Oxyethylenated lauryl alcohol ($C_{12}$–$C_{14}$/55–45%) containing 12 mol of ethylene oxide ($nC_a$ = 12.5 – HLB = 14) | 8 g |
| Cetyl/stearyl ($C_{16}$/$C_{18}$ - 50:50) alcohol ($nC_B$ = 17 – HLB = 1) | 5 g |
| Oxyethylenated decyl alcohol ($C_{10}$–$C_{12}$–$C_{14}$/85–8.5–6.5) containing 3.5 mol of ethylene oxide, sold by the company HENKEL under the name MERGITAL BL 309 ($nC_B$ = 10.4 – HLB = 8.5) | 22 g |
| Cationic polymer described and prepared according to French Patent 2,270,846, consisting of recurring units of formula: | 0.1 g |

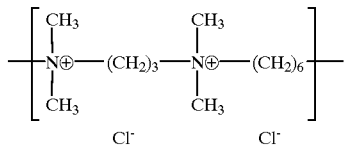

| | |
|---|---|
| Propylene glycol | 6 g |
| Aqueous ammonia solution containing 20% of $NH_3$ | 10 g |
| para-Phenylenediamine | 0.4 g |
| m-Aminophenol | 0.5 g |
| Hydroquinone | 0.1 g |
| 1-Phenyl-3-methyl-5-pyrazolone | 0.1 g |
| Aqueous sodium bisulfite solution containing 35% of AS | 1.3 g |
| Perfume, sequestering agent qs | |
| Water qs | 100 g |
| pH = 11.0 | |

EXAMPLE 2

| | |
|---|---|
| Oxyethylenated oleocetyl alcohol containing 30 mol of ethylene oxide ($nC_A$ = 17 – HLB = 16.5) | 7 g |
| Oxyethylenated lauryl alcohol ($C_{12}$–$C_{14}$/55–45%) containing 12 mol of ethylene oxide ($nC_A$ = 12.5 – HLB = 14) | 8 g |
| Cetyl/stearyl ($C_{16}$/$C_{18}$ - 50:50) alcohol ($nC_B$ = 17 – HLB = 1) | 5 g |
| Oxyethylenated decyl alcohol ($C_{10}$–$C_{12}$–$C_{14}$/85–8.5–6.5) containing 3.5 mol of ethylene oxide, sold by the company HENKEL under the name MERGITAL BL 309 ($nC_B$ = 10.4 – HLB = 8.5) | 22 g |
| Cationic polymer described and prepared according to French Patent 2,270,846, consisting of recurring units of formula: | 8 g |

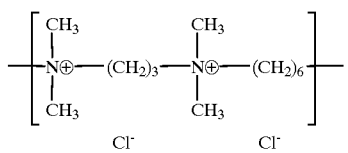

| | |
|---|---|
| Propylene glycol | 6 g |
| Aqueous ammonia solution containing 20% of $NH_3$ | 10 g |

-continued

| | |
|---|---|
| para-Phenylenediamine | 0.4 g |
| m-Aminophenol | 0.5 g |
| Hydroquinone | 0.1 g |
| 1-Phenyl-3-methyl-5-pyrazolone | 0.1 g |
| Aqueous sodium bisulfite solution containing 35% of AS | 1.3 g |
| Perfume, sequestering agent qs | |
| Water qs | 100 g |
| pH = 10.9 | |

EXAMPLE 3

| | |
|---|---|
| Oxyethylenated oleocetyl alcohol containing 30 mol of ethylene oxide ($nC_A$ = 17 – HLB = 16.5) | 7 g |
| Oxyethylenated lauryl alcohol ($C_{12}$–$C_{14}$/55–45%) containing 12 mol of ethylene oxide ($nC_A$ = 12.5 – HLB = 14) | 8 g |
| Cetyl/stearyl ($C_{16}$/$C_{18}$ - 50:50) alcohol ($nC_B$ = 17 – HLB = 1) | 5 g |
| Oxyethylenated decyl alcohol ($C_{10}$–$C_{12}$–$C_{14}$/85–8.5–6.5) containing 3.5 mol of ethylene oxide, sold by the company HENKEL under the name MERGITAL BL 309 ($nC_B$ = 10.4 – HLB = 8.5) | 22 g |
| Copolymer of diallyldimethylammonium chloride and acrylic acid, sold by the company CALGON under the name MERQUAT 280 containing 35% of AS | 3 g AS |
| Crosslinked polyacrylic acid sold by the company GOODRICH under the name CARBOPOL 934 (MW 3,000,000) | 0.4 g |
| Propylene glycol | 8 g |
| Monoethanolamine | 8.3 g |
| Hydroquinone | 0.1 g |
| 1-Phenyl-3-methyl-5-pyrazolone | 0.1 g |
| Aqueous sodium bisulfite solution containing 35% of AS | 1.3 g |
| para-Phenylenediamine | 0.5 g |
| m-Dihydroxybenzene | 0.4 g |
| Perfume, sequestering agent qs | |
| Water qs | 100 g |
| pH = 11.0 | |

EXAMPLE 4

| | |
|---|---|
| Oxyethylenated oleocetyl alcohol containing 30 mol of ethylene oxide ($nC_A$ = 17 – HLB = 16.5) | 10.8 g |
| Oxyethylenated lauryl alcohol ($C_{12}$–$C_{14}$/55–45%) containing 12 mol of ethylene oxide ($nC_A$ = 12.5 – HLB = 14) | 2.5 g |
| Oxyethylenated decyl alcohol ($C_{10}$–$C_{12}$–$C_{14}$/85–8.5–6.5) containing 5.5 mol of ethylene oxide, sold by the company HENKEL under the name MERGITAL BL 589 | 6.5 g |
| Oxyethylenated decyl alcohol ($C_{10}$–$C_{12}$–$C_{14}$/85–8.5–6.5) containing 3.5 mol of ethylene oxide, sold by the company HENKEL under the name MERGITAL BL 309 ($nC_B$ = 10.4 – HLB = 8.5) | 18.5 g |
| Oleyl alcohol (70% of $C_{18}$) ($nC_B$ = 17.5 – HLB = 1) | 2.25 g |
| Polymer of hydroxyethylcellulose and epichlorohydrin quaternized with trimethylamine, sold by the company UNION CARBIDE under the name JR 400 | 0.5 g |
| Propylene glycol | 8 g |
| Monoethanolamine | 8 g |
| Hydroquinone | 0.1 g |
| 1-Phenyl-3-methyl-5-pyrazolone | 0.1 g |
| Aqueous sodium bisulfite solution containing 35% of AS | 1.3 g |
| para-Phenylenediamine | 0.5 g |
| m-Dihydroxybenzene | 0.4 g |
| Perfume, sequestering agent qs | |
| Water qs | 100 g |
| pH = 11.0 | |

EXAMPLE 5

| | |
|---|---|
| Oxyethylenated oleocetyl alcohol containing 30 mol of ethylene oxide ($nC_A$ = 17 – HLB = 16.5) | 9 g |
| Oxyethylenated lauryl alcohol ($C_{12}$–$C_{14}$/55–45%) containing 12 mol of ethylene oxide ($nC_A$ = 12.5 – HLB = 14) | 7 g |
| Oxyethylenated decyl alcohol ($C_{10}$–$C_{12}$–$C_{14}$/85–8.5–6.5) containing 5.5 mol of ethylene oxide, sold by the company HENKEL under the name MERGITAL BL 589 | 12.2 g |
| Oxyethylenated decyl alcohol ($C_{10}$–$C_{12}$–$C_{14}$/85–8.5–6.5) containing 3.5 mol of ethylene oxide, sold by the company HENKEL under the name MERGITAL BL 309 ($nC_B$ = 10.4 – HLB = 8.5) | 8.8 g |
| Oleyl alcohol (70% of $C_{18}$) ($nC_B$ = 17.5 – HLB = 1) | 4 g |
| Copolymer of vinylpyrrolidone and methacrylamidopropyltrimethylammonium chloride (85:15), sold by the company GAF in aqueous solution containing 20% of AS under the name GAFQUAT HS 100 | 3 g |
| Propylene glycol | 8 g |
| Monoethanolamine | 8 g |
| Hydroquinone | 0.1 g |
| 1-Phenyl-3-methyl-5-pyrazolone | 0.1 g |
| Aqueous sodium bisulfite solution containing 35% of AS | 1.3 g |
| para-Phenylenediamine | 0.5 g |
| m-Dihydroxybenzene | 0.4 g |
| Perfume, sequestering agent qs | |
| Water qs | 100 g |
| pH = 10.9 | |

EXAMPLE 6

| | |
|---|---|
| Oxyethylenated oleocetyl alcohol containing 30 mol of ethylene oxide ($nC_A$ = 17 – HLB = 16.5) | 6 g |
| Oxyethylenated lauryl alcohol ($C_{12}$–$C_{14}$/55–45%) containing 12 mol of ethylene oxide ($nC_A$ = 12.5 – HLB = 14) | 10 g |
| Polyglycerolated oleyl alcohol containing 2 mol of glycerol ($nC_B$ = 18 – HLB = 7.1) | 10 g |
| Cetyl/stearyl ($C_{16}$/$C_{18}$-50:50) alcohol ($nC_B$ = 17 – HLB = 1) | 11 g |
| Cationic polymer described and prepared according to French Patent 2,270,846, consisting of recurring units of formula | 3 g |

-continued

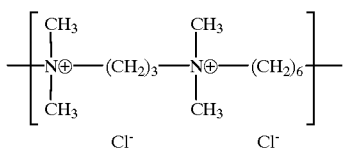

| | |
|---|---|
| Propylene glycol | 8 g |
| Triethanolamine | 0.1 g |
| Hydroquinone | 0.1 g |
| 1-Phenyl-3-methyl-5-pyrazolone | 0.1 g |
| Aqueous sodium bisulfite solution containing 35% of As | 1.3 g |
| para-Phenylenediamine | 0.5 g |
| m-Dihydroxybenzene | 0.4 g |
| Perfume, sequestering agent qs | |
| Water qs | 100 g |
| pH = 6 | |

EXAMPLE 7

| | |
|---|---|
| Oxyethylenated isostearyl alcohol containing 2.0 mol of ethylene oxide ($nC_A = 18 - HLB = 14.9$) | 24 g |
| Oxyethylenated isostearyl alcohol containing 2 mol of ethylene oxide ($nC_B = 18 - HLB = 6.5$) | 20 g |
| Cationic polymer described and prepared according to French Patent 2,270,846, consisting of recurring units of formula | 3 g |

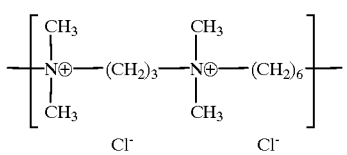

| | |
|---|---|
| Propylene glycol | 20 g |
| Monoethanolamine | 8 g |
| Hydroquinone | 0.1 g |
| 1-Phenyl-3-methyl-5-pyrazolone | 0.1 g |
| Aqueous sodium bisulfite solution containing 35% of As | 1.3 g |
| para-Phenylenediamine | 0.5 g |
| m-Dihydroxybenzene | 0.4 g |
| Perfume, sequestering agent qs | |
| Water qs | 100 g |
| pH = 10.9 | |

EXAMPLE 8

| | |
|---|---|
| Oxyethylenated oleocetyl alcohol containing 30 mol of ethylene oxide ($nC_A = 17 - HLB = 16.5$) | 6 g |
| Oxyethylenated lauryl alcohol ($C_{12}$–$C_{14}$/55–45%) containing 12 mol of ethylene oxide ($nC_A = 12.5 - HLB = 14$) | 10 g |
| Cetyl/stearyl ($C_{16}$/$C_{18}$ - 50:50) alcohol ($nC_B = 17 - HLB = 1$) | 11 g |
| Oxyethylenated decyl alcohol ($C_{10}$–$C_{12}$–$C_{14}$/85–8.5–6.5) containing 3.5 mol of ethylene oxide, sold by the company HENKEL under the name MERGITAL BL 309 ($nC_B = 10.4 - HLB = 8.5$) | 10 g |
| Hydrophobic silica sold by the company DEGUSSA under the name AEROSIL R 972 | 2 g |

-continued

| | |
|---|---|
| Cationic polymer described and prepared according to French Patent 2,270,846, consisting of recurring units of formula: | 3 g |

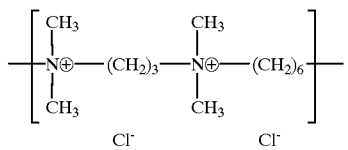

| | |
|---|---|
| Propylene glycol | 8 g |
| Monoethanolamine | 8 g |
| Lauric acid (neutralized with 0.5 g of monoethanolamine) | 2 g |
| Hydroquinone | 0.1 g |
| 1-Phenyl-3-methyl-5-pyrazolone | 0.1 g |
| Aqueous sodium bisulfite solution containing 35% of AS | 1.3 g |
| para-Phenylenediamine | 0.5 g |
| m-Dihydroxybenzene | 0.4 g |
| Perfume, sequestering agent qs | |
| Water qs | 100 g |
| pH = 10.9 | |

EXAMPLE 9

| | |
|---|---|
| Oxyethylenated oleocetyl alcohol containing 30 mol of ethylene oxide ($nC_A = 17 - HLB = 16.5$) | 3.9 g |
| Oxyethylenated lauryl alcohol ($C_{12}$–$C_{14}$/55–45%) containing 12 mol of ethylene oxide ($nC_A = 12.5 - HLB = 14$) | 6.6 g |
| Oxyethylenated decyl alcohol ($C_{10}$–$C_{12}$–$C_{14}$/85–8.5–6.5) containing 5.5 mol of ethylene oxide, sold by the company HENKEL under the name MERGITAL BL 589 | 6.6 g |
| Oxyethylenated decyl alcohol ($C_{10}$–$C_{12}$–$C_{14}$/85–8.5–6.5) containing 3.5 mol of ethylene oxide, sold by the company HENKEL under the name MERGITAL BL 309 ($nC_B = 10.4 - HLB = 8.5$) | 22 g |
| Oleyl alcohol (70% of $C_{18}$) ($nC_B = 17.5 - HLB = 1$) | 1.1 g |
| Cationic polymer described and prepared according to French Patent 2,270,846, consisting of recurring units of formula: | 2.1 g |

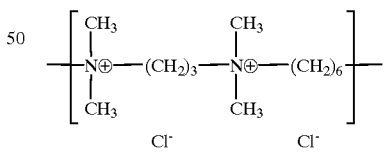

| | |
|---|---|
| Copolymer of diallyldimethylammonium chloride and acrylic acid, sold by the company CALGON under the name MERQUAT 280 containing 35% of AS | 1.4 g AS |
| Crosslinked polyacrylic acid sold by the company GOODRICH under the name CARBOPOL 934 (MW 3,000,000) | 0.4 g |
| Propylene glycol | 8 g |
| Monoethanolamine | 8 g |
| Hydroquinone | 0.1 g |
| 1-Phenyl-3-methyl-5-pyrazolone | 0.1 g |
| Aqueous sodium bisulfite solution containing 35% of AS | 1.3 g |
| para-Phenylenediamine | 0.5 g |

| | |
|---|---|
| m-Dihydroxybenzene | 0.4 g |
| Perfume, sequestering agent qs | |
| Water qs | 100 g |
| pH = 11 | |

EXAMPLE 10

| | |
|---|---|
| Oxyethylenated isostearyl alcohol containing 20 mol of ethylene oxide ($nC_A$ = 18 – HLB = 14.9) | 8 g |
| Oxyethylenated isostearyl alcohol containing 2 mol of ethylene oxide ($nC_B$ = 18 – HLB = 6,5) | 7 g |
| Quaternized cellulose ether derivative sold by the company UNION CARBIDE under the name POLYMER JR 30 M | 2 g |
| Propylene glycol | 3 g |
| Ammonia solution (20% of $NH_3$) | 5 g |
| Hydroquinone | 0.1 g |
| 1-Phenyl-3-methyl-5-pyrazolone | 0.1 g |
| Aqueous sodium bisulfite solution containing 35% of AS | 1.3 g |
| para-Phenylenediamine | 0.5 g |
| m-Dihydroxybenzene | 0.4 g |
| Perfume, sequestering agent qs | |
| Water qs | 100 g |
| pH = 11 | |

The compositions of Examples 1 to 10 are stable on storage.

At the time of use, they are diluted with an equal volume of "20 volumes" hydrogen peroxide. It is possible to use either a "20 volumes" aqueous hydrogen peroxide solution at pH 3, or one of the two oxidizing emulsions below.

| | | |
|---|---|---|
| a) | Cetyl alcohol | 1.5 g |
| | Oxyethylenated cetyl/stearyl alcohol containing 15 mol of ethylene oxide | 2.5 g |
| | ortho-oxyquinoline sulfate | 0.05 g |
| | Hydrogen peroxide, "200 vol.", qs | 20 vol |
| | HCl qs pH 3 | |
| | Water qs | 100 g |
| b) | Oxyethylenated cetyl/stearyl alcohol sold by the company HENKEL under the name SINNOWAX | 4 g |
| | ortho-oxyquinoline sulfate | 0.05 g |
| | Hydrogen peroxide, "200 vol.", qs | 20 vol |
| | HCl qs pH 3 | |
| | Water qs | 100 g |

When applied to bleached hair for 30 minutes at room temperature, the compositions of Examples 1 and 2 impart a purple-gray color to the hair, whereas the compositions of Examples 3 to 10 dye it ash chestnut-brown.

EXAMPLE 11

| Dyeing composition | |
|---|---|
| Oxyethylenated oleocetyl alcohol containing 30 mol of ethylene oxide ($nC_A$ = 17 – HLB = 16.5) | 4.2 g |
| Oxyethylenated lauryl alcohol ($C_{12}$–$C_{14}$/55–45%) containing 12 mol of ethylene oxide ($nC_A$ = 12.5 – HLB = 14) | 4.8 g |
| Cetyl/stearyl ($C_{16}$/$C_{18}$ - 50:50) alcohol ($nC_B$ = 17 – HLB = 1) | 3 g |
| Oxyethylenated decyl alcohol ($C_{10}$–$C_{12}$–$C_{14}$/85–8.5–6.5) containing 3.5 mol of ethylene oxide, sold by the company HENKEL under the name MERGITAL BL 309 ($nC_B$ = 10.4 – HLB = 8.5) | 13.2 g |
| Homopolymer of diallyldimethylammonium chloride, sold by the company MERCK under the name MERQUAT 100 containing 40% of AS | 3 g AS |
| Aqueous ammonia solution containing 20% of $NH_3$ | 12 g |
| para-Phenylenediamine | 0.45 g |
| m-Dihydroxybenzene | 0.35 g |
| Aqueous sodium bisulfite solution containing 35% of AS | 1.8 g |
| Perfume, sequestering agent qs | |
| Water qs | 100 g |
| pH = 10.9 | |

When applied as described above to natural white hair, the composition imparts a chestnut-brown coloration to the hair.

EXAMPLE 12

| Dyeing composition | |
|---|---|
| Oleic acid | 3 g |
| Oxyethylenated oleocetyl alcohol containing 30 mol of ethylene oxide ($nC_A$ = 17 – HLB = 16.5) | 7 g |
| Oxyethylenated lauryl alcohol ($C_{12}$–$C_{14}$/55–45%) containing 12 mol of ethylene oxide ($nC_A$ = 12.5 – HLB = 14) | 8 g |
| Oxyethylenated decyl alcohol ($C_{10}$–$C_{12}$–$C_{14}$/85–8.5–6.5) containing 3.5 mol of ethylene oxide, sold by the company HENKEL under the name MERGITAL BL 309 ($nC_B$ = 10.4 – HLB = 8.5) | 22 g |
| Oleyl alcohol (70% of $C_{18}$) ($nC_B$ = 17.5 – HLB = 1) | 5 g |
| Homopolymer of diallyldimethylammonium chloride, sold by the company MERCK under the name MERQUAT 100 containing 40% of AS | 1.5 g AS |
| Copolymer of diallyldimethylammonium chloride and acrylic acid, sold by the company CALGON under the name MERQUAT 280 containing 35% of AS | 1.5 g AS |
| para-Phenylenediamine | 0.3 g |
| m-Aminophenol | 0.15 g |
| Aqueous sodium bisulfite solution containing 35% of AS | 1.3 g |
| Aqueous ammonia solution containing 20% of $NH_3$ | 12 g |
| Perfume, sequestering agent qs | |
| Water qs | 100 g |
| pH = 10.9 | |

When applied as described above to permanent-waved white hair, the coloration obtained is deep purple-gray.

EXAMPLE 13

| Dyeing composition | |
|---|---|
| Oxyethylenated oleocetyl alcohol containing 30 mol of ethylene oxide ($nC_A$ = 17 – HLB = 16.5) | 7 g |
| Oxyethylenated lauryl alcohol ($C_{12}$–$C_{14}$/55–45%) containing 12 mol of ethylene oxide ($nC_A$ = 12.5 – HLB = 14) | 8 g |
| Cetyl/stearyl ($C_{16}$/$C_{18}$ - 50:50) alcohol ($nC_B$ = 17 – HLB = 1) | 5 g |
| Oxyethylenated decyl alcohol ($C_{10}$–$C_{12}$–$C_{14}$/85–8.5–6.5) containing 3.5 mol of ethylene oxide, sold by the company HENKEL under the name MERGITAL BL 309 ($nC_B$ = 10.4 – HLB = 8.5) | 22 g |
| Cationic polymer described and prepared according to French Patent 2,270,846, consisting of recurring units of formula: | 8 g |

$$\left[ -\underset{\underset{CH_3}{|}}{\overset{\overset{CH_3}{|}}{N^{\oplus}}} -(CH_2)_3 -\underset{\underset{CH_3}{|}}{\overset{\overset{CH_3}{|}}{N^{\oplus}}} -(CH_2)_6 - \right]$$
$$Cl^- \quad\quad Cl^-$$

| | |
|---|---|
| Propylene glycol | 6 g |
| Aqueous ammonia solution containing 20% of $NH_3$ | 15 g |
| Perfume, sequestering agent qs | |
| Water qs | 100 g |
| pH = 10.9 | |

What is claimed is:

1. Method for hair dyeing or bleaching using a composition which contains, in a cosmetically acceptable medium:
    a) 14 to 50% of a mixture of nonionic surfactants, the nonionic surfactants being fatty alcohols, oxyethylenated fatty alcohols, oxypropylenated fatty alcohols, polyglycerolated fatty alcohols whose fatty chain contains from 10 to 50 carbon atoms which are linear or branched, the mixture comprising at least one surfactant A whose HLB value is from 14 to 18.8, present at a weight concentration [A], surfactant A being a mixture of oxyethylenated fatty alcohols whose fatty chain contains from 12 to 30 carbon atoms, and a nonionic surfactant B whose HLB value as defined by Griffin is from 1 to 9.7, present in a weight quantity [B], surfactant B being a mixture of fatty alcohols whose fatty chain contains from 10 to 50 carbon atoms and oxyethylenated fatty alcohols whose fatty chain contains from 10 to 50 carbon atoms, said nonionic surfactants A and B satisfying the inequality:

$$0.5 \leq R \leq 1.6$$

in which R denotes the ratio $$R = \frac{\sum (nC_A \times [A])}{\sum (nC_B \times [B])}$$

in which:
    $nC_A$ is the number of carbon atoms in the fatty chain of the surfactant A and $nC_B$ the number of carbon atoms in the fatty chain of the surfactant B; and
    b) 0.05 to 10% of a cationic or amphoteric substantive polymer, the substantive polymer is:

a quaternized protein consisting of a chemically modified polypeptide bearing a quaternary ammonium group at the end of the chain or grafted onto the latter;

a cationic polysiloxane;

a polyamine, polyaminoamide; a cyclopolymer having a molecular weight of 20,000 to 3,000,000 which is a homopolymer containing as main constituent of the chain units corresponding to the formulae (II) or (II'):

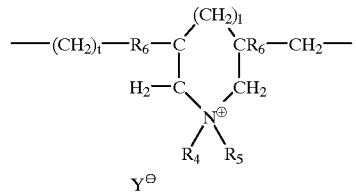

(II)

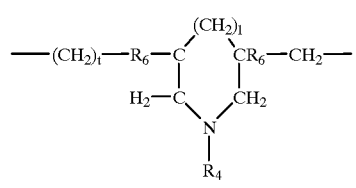

(II')

l and t are equal to 0 or 1, and the sum l+t=1;

$R_6$ denotes hydrogen or methyl;

$R_4$ and $R_5$ denote, independently of one another, an alkyl group having from 1 to 22 carbon atoms, a hydroxyalkyl group in which the alkyl group has 1 to 5 carbon atoms or a lower amidoalkyl group, and where $R_4$ and $R_5$ jointly with the nitrogen atom to which they are attached, can denote a heterocyclic group as well as copolymers containing units of formulae (II) or (II') and units derived from acrylamide or from diacetoneacrylamide;

$Y^{\ominus}$ is an anion;

a poly(quaternary ammonium) polymer containing recurring units corresponding to the formula:

(III)

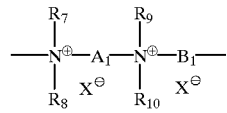

in which $R_7$ and $R_8$, $R_9$ and $R_{10}$, being identical or different, represent aliphatic, alicyclic or acrylaliphatic radicals containing from 1 to 20 carbon atoms or lower hydroxyalkylaliphatic radical, or alternatively $R_7$ and $R_8$ and $R_9$ and $R_{10}$, together or separately and with the nitrogen atoms to which they are attached, constitute heterocyclic optionally containing a second hetero atom other than nitrogen, or alternatively $R_7$, $R_8$, $R_9$ and $R_{10}$ represent a linear or branched $C_1$–$C_4$ alkyl radical substituted with nitrile, ester, acyl or amide group or a group $$-\overset{O}{\underset{\|}{C}}-O-OR_{11}-D \quad \text{or} \quad -\overset{O}{\underset{\|}{C}}-NH-R_{11}-D$$

where $R_{11}$ is an alkylene and D a quaternary ammonium group;

$A_1$ and $B_1$ represent polymethylene containing from 2 to 20 atoms, and $X^{\ominus}$ denotes an anion derived from an inorganic or organic acid, $A_1$ and $R_7$ and $R_9$, with the two nitrogen atoms to which they are attached, can form a piperazine ring; in addition, if $A_1$ denotes a saturated or unsaturated, linear or branched alkylene or hydroxyalkylene radical, $B_1$ can also denote a group $$(CH_2)_n-CO-D-OC-(CH_2)_n-$$

in which D denotes:
(i) a glycol residue of formula: —O—Z—O— where Z denotes a linear or branched hydrocarbon radical or a group corresponding to the formulae:

$$-[CH_2-CH_2-O]_x CH_2-CH_2-$$
$$-[CH_2-CH-O]_y CH_2-CH-$$
$$\qquad\quad |\qquad\qquad\quad\;\; |$$
$$\qquad\quad CH_3\qquad\qquad CH_3$$

where x and y denote an integer from 1 to 4, representing a defined and unique degree of polymerization, or any number from 1 to 4 representing an average degree of polymerization;
(ii) a bis-secondary diamine residue such as a piperazine derivative;
(iii) a bis-secondary diamine of formula:

—NH—Y—NH— where Y denotes a linear or branched hydrocarbon radical or alternatively the divalent radical $$-CH_2-CH_2-S-S-CH_2-CH_2-$$

X— is an anion;
the poly(quaternary ammonium) polymers consisting of units of formula:

(IV)

$$-\overset{R_{12}}{\underset{\underset{X^{\ominus}}{R_{13}}}{N^{\oplus}}}-(CH_2)_x-NH-\overset{O}{\underset{\|}{C}}-(CH_2)_m-\overset{O}{\underset{\|}{C}}-NH-(CH_2)_y-\overset{R_{14}}{\underset{\underset{X^{\ominus}}{R_{15}}}{N^{\oplus}}}-A-$$

in which
$R_{12}, R_{13}, R_{14}$ and $R_{15}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH radical, where p is equal to 0 or an integer between 1 and 6, with the proviso that $R_{12}, R_{13}, R_{14}$ and $R_{15}$ do not simultaneously represent a hydrogen atom;

x and y, which may be identical or different, are integers between 1 and 6;

m is equal to 0 or to an integer between 1 and 34;

x denotes a halogen atom;

A denotes a radical of a dihalide;

the poly(quaternary ammonium) polymers consisting of units of formula IVa:

$$\left[\begin{array}{c} CH_3 \\ | \\ N^{\oplus}-CH_3 \\ | \\ (CH_2)_3 \\ | \\ NH \\ | \\ C=O \\ | \\ NH \\ | \\ (CH_2)_3 \\ | \\ CH_3-N^{\oplus}-CH_2CH_2OCH_2CH_2- \\ | \\ CH_3 \end{array}\right]$$

the poly(quaternary ammonium) polymers consisting of units of formula IVb:

$$\left[\begin{array}{c} CH_3 \\ | \\ -N^{\oplus}-(CH_2)_3NH-\overset{O}{\underset{\|}{C}}-(CH_2)_4-\overset{O}{\underset{\|}{C}}-NH-(CH_2)_3 \\ | \qquad\qquad\qquad\qquad\qquad\qquad\qquad\qquad\qquad | \\ CH_3 \qquad\qquad\qquad\qquad\qquad CH_3-N^{\oplus}-CH_3 \\ \qquad\qquad\qquad\qquad\qquad\qquad\qquad\qquad\qquad | \\ \qquad\qquad\qquad\qquad\qquad\qquad\qquad\qquad\qquad CH_2 \\ \qquad\qquad\qquad\qquad\qquad\qquad\qquad\qquad\qquad | \\ \qquad\qquad\qquad\qquad\qquad\qquad\qquad\qquad\qquad CH_2 \\ \qquad\qquad\qquad\qquad\qquad\qquad\qquad\qquad\qquad | \\ \qquad\qquad\qquad\qquad\qquad\qquad\qquad\qquad\qquad O-CH_2-CH_2- \end{array}\right]$$

the poly(quaternary ammonium) polymers consisting of units of formula IVc:

$$\left[\begin{array}{c} CH_3 \\ | \\ -N^{\oplus}-(CH_2)_3-NH-\overset{O}{\underset{\|}{C}}-(CH_2)_7-\overset{O}{\underset{\|}{C}}-NH-(CH_2)_3 \\ | \qquad\qquad\qquad\qquad\qquad\qquad\qquad\qquad\qquad | \\ CH_3 \qquad\qquad\qquad\qquad\qquad CH_3-N^{\oplus}-CH_3 \\ \qquad\qquad\qquad\qquad\qquad\qquad\qquad\qquad\qquad | \\ \qquad\qquad\qquad\qquad\qquad\qquad\qquad\qquad\qquad CH_2 \\ \qquad\qquad\qquad\qquad\qquad\qquad\qquad\qquad\qquad | \\ \qquad\qquad\qquad\qquad\qquad\qquad\qquad\qquad\qquad CH_2 \\ \qquad\qquad\qquad\qquad\qquad\qquad\qquad\qquad\qquad | \\ \qquad\qquad\qquad\qquad\qquad\qquad\qquad\qquad\qquad O-CH_2-CH_2- \end{array}\right]$$

the poly(quaternary ammonium) polymers formed by the reaction of polymer of formula IVa with polymer of formula IVb;

homopolymers or copolymers derived from acrylic or methacrylic esters or amides and containing the units

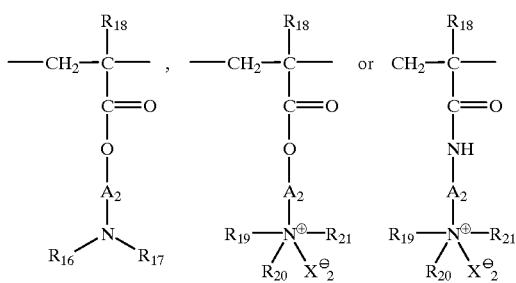

(V)

in which $R_{18}$ denotes H or $CH_3$;

$A_2$ is a linear or branched alkyl group containing 1 to 6 carbon atoms or a hydroxyalkyl group containing 1 to 4 carbon atoms;

$R_{19}$, $R_{20}$ and $R_{21}$, which may be identical or different, represent an alkyl group having from 1 to 18 carbon atoms or a benzyl radical; $R_{16}$ and $R_{17}$ represent hydrogen or an alkyl group having from 1 to 6 carbon atoms;

$X^\ominus_2$ denotes a methosulfate anion or a halide, the comonomer(s) belong to the family comprising acrylamide, methacrylamide, diacetoneacrylamide, acrylamide and methacylamide substituted on the nitrogen with lower alkyl groups, acrylic or methacrylic acids or their esters, vinylpyrrolidone, vinyl esters;

the composition being stable at room temperature and at a pH above or equal to 5.5, comprising applying the composition to hair as an oxidative hair dyeing or bleaching vehicle compositions.

2. The method of claim 1, wherein the dihalide represents

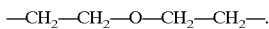

3. Method as claimed in claim 1, in which the surfactants are present in the composition in a proportion of between 20 and 50%.

4. Method as claimed in claim 1, in which the nonionic surfactants present in the composition contain less than 48% of surfactants not corresponding to the definition of the surfactants A and B.

5. Method as claimed in claim 1, in which the nonionic surfactants other than the surfactants A and B have an HLB value of between 10 and 14.

6. Method as claimed in claim 1, in which the type A surfactants having an HLB value from 14 to 18.8 are chosen from oxyethylenated oleocetyl alcohol containing 30 mol of ethylene oxide, oxyethylenated lauryl alcohol ($C_{12}$–$C_{14}$/55–45%) containing 12 mol of ethylene oxide, oxyethylenated lauryl alcohol containing 23 mol of ethylene oxide, oxyethylenated stearyl alcohol containing 100 mol of ethylene oxide, oxyethylenated isostearyl alcohol containing 20 mol of ethylene oxide, oxyethylenated behenyl alcohol containing 20 mol of ethylene oxide, oxyethylenated $C_{30}$ primary alcohol containing 40 mol of ethylene oxide, oxyethylenated octylphenols containing 11 to 50 mol of ethylene oxide, oxyethylenated nonylphenols containing 12 to 50 mol of ethylene oxide and oxyethylenated cetyl/stearyl alcohol containing 15 mol of ethylene oxide.

7. Method as claimed in claim 1, in which the type B nonionic surfactants having an HLB value from 1 to 9.7 are chosen from oxyethylenated decyl alcohol containing 3.5 mol of ethylene oxide, oleyl alcohol containing 70% of $C_{18}$, lauryl alcohol, cetyl/stearyl (50:50) alcohol, oxyethylenated isostearyl alcohol containing 2 mol of ethylene oxide, oxyethylenated oleyl alcohol containing 3 mol of ethylene oxide, oxyethylenated lauryl alcohol containing 4 mol of ethylene oxide, oxyethylenated C_primary alcohol containing 4 mol of ethylene oxide, oxyethylenated octylphenols containing less than 4.5 mol of ethylene oxide, oxyethylenated nonylphenols containing less than 5 mol of ethylene oxide or oxyethylenated $C_{50}$ primary alcohol containing 4 mol of ethylene oxide.

8. Method as claimed in claim 1, in which the nonionic surfactants and other than the surfactants A and B are chosen from oxyethylenated decyl alcohol containing 5.5 mol of ethylene oxide, oxyethylenated nonylphenol containing 6 mol of ethylene oxide or oxyethylenated $C_{30}$ primary alcohol containing 10 mol of ethylene oxide.

9. Method as claimed in claim 1, in which the substantive polymers are chosen from polymers containing primary, secondary, tertiary or quaternary amine groups or mixtures thereof, forming part of the polymer chain or linked directly to the polymer chain, and having a molecular weight of between 500 and approximately 5,000,000.

10. Method as claimed in claim 9, wherein the substantive polymers have a molecular weight between 1,000 and 3,000,000.

11. Method as claimed in claim 1, which contains alkalinizing agents, preservatives, sequestering agents, perfumes, sunscreen agents, fatty amides, natural or synthetic sterols, $C_{10}$–$C_{18}$ fatty acids, polymers other than substantive polymers or thickeners that do not destabilize the composition.

12. Method as claimed in claim 1, in which the cosmetically acceptable medium is an aqueous medium or a mixture of water and a water-miscible organic solvent.

13. Method as claimed in claim 1, in which solvents are lower aliphatic alcohols, glycols, glycol ethers, or mixtures thereof.

14. A hair dyeing composition, which consists of a composition which contains, in a cosmetically acceptable medium:

a) 14 to 50% of a mixture of nonionic surfactants chosen from fatty alcohols, oxyethylenated fatty alcohols, oxypropylenated fatty alcohols, polyglycerolated fatty alcohols or mixture thereof which are linear or branched, the mixture comprising at least one surfactant A whose HLB value as defined by Griffin is from 14 to 18.8, present at a weight concentration [A], surfactant A being a mixture of oxyethylenated fatty alcohols whose fatty chain contains a number of carbon atoms from 12 to 30, and a nonionic surfactant B whose HLB value as defined by Griffin is from 1 to 9.7, present in a weight quantity [B], surfactant B being a mixture of fatty alcohols whose fatty chain contains a number of carbon atoms from 10 to 50 and oxyethylenated fatty alcohols whose fatty chain contains a number of carbon atoms from 10 to 50, said nonionic surfactants A and B satisfying the inequality:

$0.5 \leq R \leq 1.6$ in which R denotes the ratio $$R = \frac{\sum (nC_A \times [A])}{\sum (nC_B \times [B])}$$

in which:
nC$_A$ is the number of carbon atoms in the fatty chain of the surfactant A and nC$_B$ the number of carbon atoms in the fatty chain of the surfactant B; and b) 0.05 to 10% of a cationic or amphoteric substantive polymer, the composition being stable at room temperature and at a pH above or equal to 5.5, and which contains one or more oxidation dye precursors and/or one or more indole dyes generating melanin type pigments under the action of an oxidizing agent.

15. The composition as claimed in claim 14, which composition also contains direct dyes.

16. A hair dyeing process, wherein the composition as defined in claim 14, containing one or more oxidation dye precursors and diluted at the time of use with an oxidizing composition, is applied to this hair in a sufficient quantity to produce a coloration, wherein the composition is allowed to act for a period of between 5 and 45 minutes approximately, and wherein the hair is rinsed.

17. A bleaching composition, which consists of a composition which contains, in a cosmetically acceptable medium:

a) 14 to 50% of a mixture of nonionic surfactants chosen from fatty alcohols, oxyethylenated fatty alcohols, oxypropylenated fatty alcohols, polyglyercolated fatty alcohols or mixture thereof which are linear or branched, the mixture comprising at least one surfactant A whose HLB value as defined by Griffin is from 14 to 18.8, present at a weight concentration [A], surfactant A being a mixture of oxyethylenated fatty alcohols whose fatty chain contains a number of carbon atoms from 12 to 30, and a nonionic surfactant B whose HLB value as defined by Griffin is from 1 to 9.7, present in a weight quantity [B], surfactant B being a mixture of fatty alcohols whose fatty chain contains a number of atoms from 10 to 50 and oxyethylenated fatty alcohols whose fatty chain contains a number of atoms from 10 to 50, said nonionic surfactants A and B satisfying the inequality:

$$0.5 \leq R \leq 1.6$$

in which R denotes the ratio $$R = \frac{\sum (nC_A \times [A])}{\sum (nC_B \times [B])}$$

in which:
nC$_A$ is the number of carbon atoms in the fatty chain of the surfactant A and nC$_B$ the number of carbon atoms in the fatty chain of the surfactant B; and b) 0.05 to 10% of a cationic or amphoteric substantive polymer, the composition being stable at room temperature and at a pH above or equal to 5.5, and which contains a hair bleaching agent, added at the time of use.

18. A hair bleaching process, wherein the bleaching composition defined in claim 17 is applied to the hair in a sufficient quantity and for a sufficient period to bleach the hair, and wherein the hair is then rinsed.

19. The composition as claimed in claim 18, in which the bleaching agent is hydrogen peroxide, a persulfate, a perborate or a sodium percarbonate.

\* \* \* \* \*